United States Patent [19]

Hodge

[11] Patent Number: 4,767,403
[45] Date of Patent: Aug. 30, 1988

[54] POSITIVE PULSE DEVICE AND SYSTEM
[75] Inventor: Colin G. Hodge, Columbia, Md.
[73] Assignee: The BOC Group, Inc., Montvale, N.J.
[21] Appl. No.: 12,520
[22] Filed: Feb. 9, 1987
[51] Int. Cl.$^4$ .............................................. A61M 1/00
[52] U.S. Cl. ..................................... 604/35; 604/120; 137/495
[58] Field of Search ...................... 604/31, 33, 35, 73, 604/119, 120, 135; 137/495, 624.13, 103; 251/61.5

[56]  References Cited
U.S. PATENT DOCUMENTS

| | | | |
|---|---|---|---|
| 1,874,293 | 8/1932 | Hook et al. | 137/495 |
| 2,746,471 | 5/1956 | Cobb | 251/61.5 |
| 3,741,240 | 6/1973 | Berriman | 137/495 |
| 4,391,260 | 7/1983 | Asahi | 137/907 |

Primary Examiner—C. Fred Rosenbaum
Assistant Examiner—J. L. Kruter
Attorney, Agent, or Firm—Larry R. Cassett; Roger M. Rathbun

[57]  ABSTRACT

A catheter pulse device is disclosed which is activated by vacuum signals and which is used adjacent to or directly attached to a catheter for withdrawing fluids from a patient's body cavity, such as the stomach. The device operates immediately following the normal cessation of suction in an intermittent suction system and returns a minute quantity of the withdraw fluid back into the catheter itself to clear the withdrawal passageways. The pulse device provides protection against an excess of vacuum from reaching the patients cavity by utilizing a specially designed valve that opens and closes the path between a source of regulated vacuum and the patient. That valve is balanced such that it initially opens at or approximately at the point the vacuum on the patient side of the valve reaches the regulated vacuum set by the doctor or other knowledgeable personnel, and thus the vacuum to the patient does not exceed a set amount. The pulse device can therefore be used in a system where the device itself is located directly on or adjacent the catheter itself, thus eliminating long distensible passageways between the pulse device and the patient and thereby minimizing the detrimental reservoir effect of such long passageways.

14 Claims, 4 Drawing Sheets

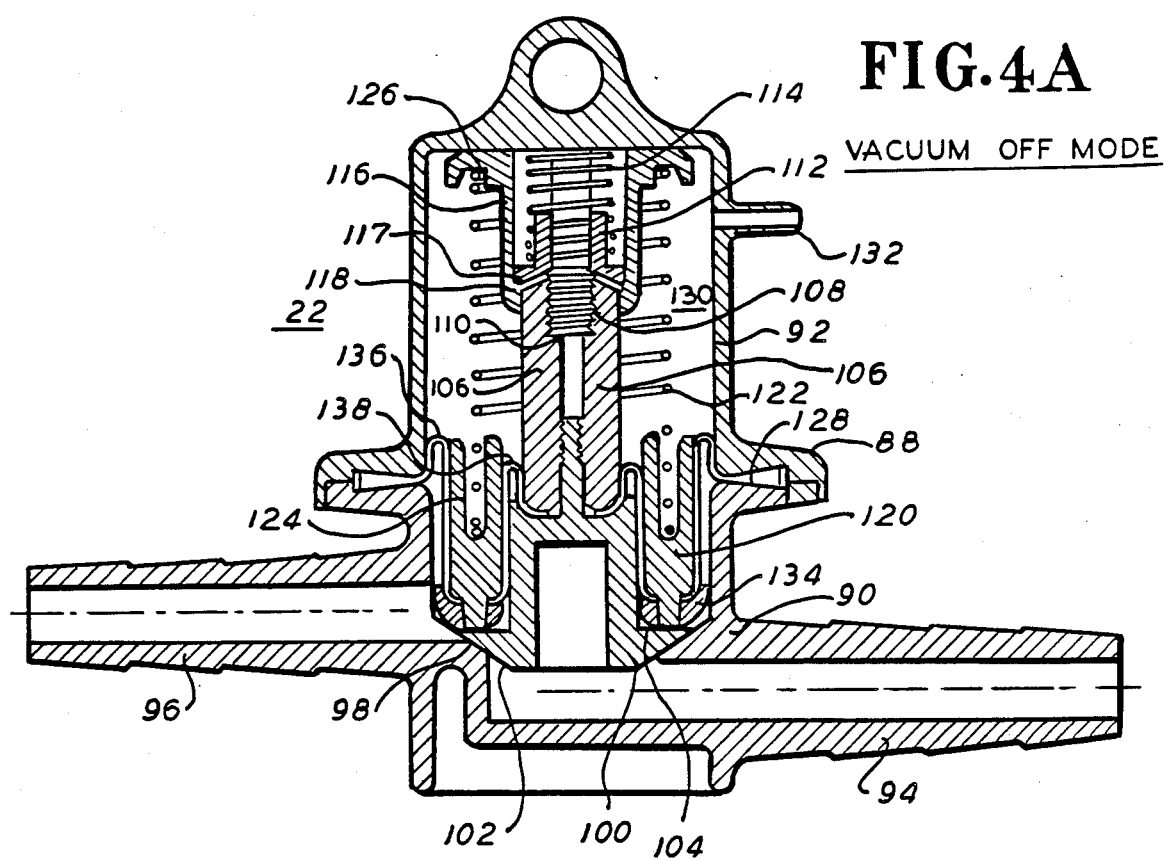
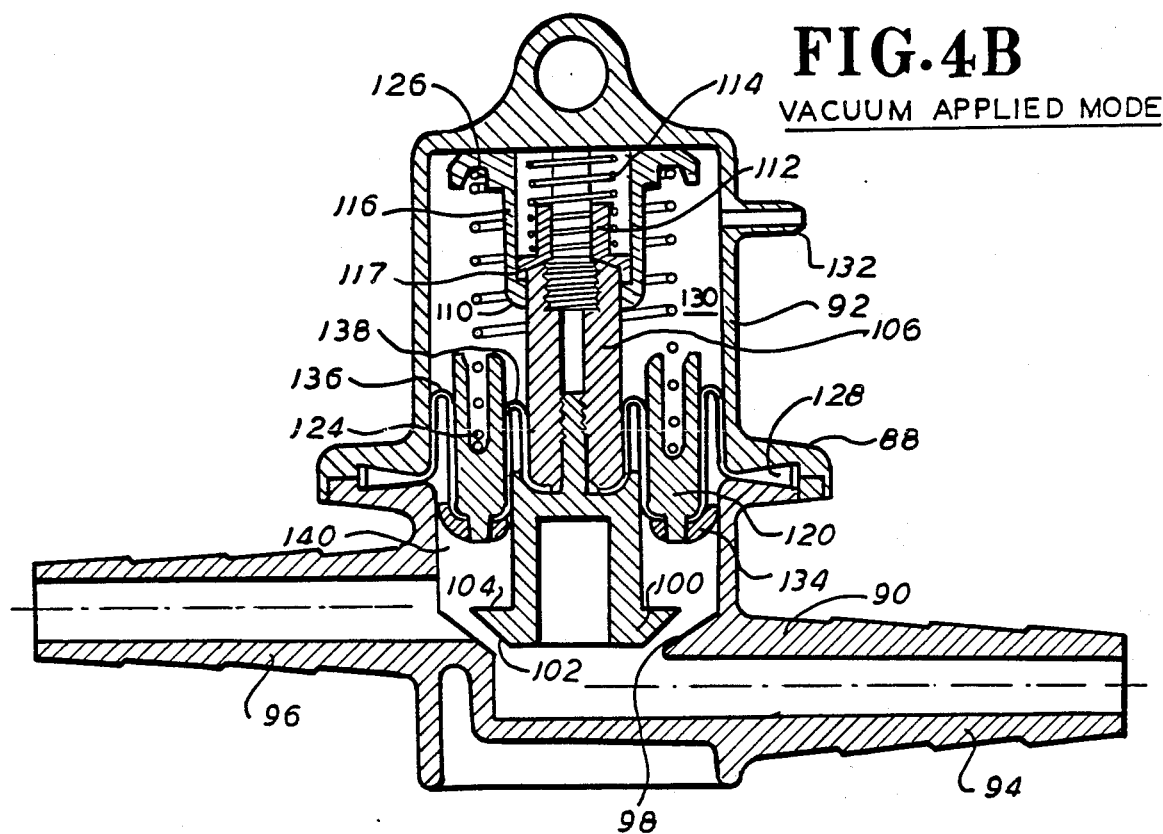

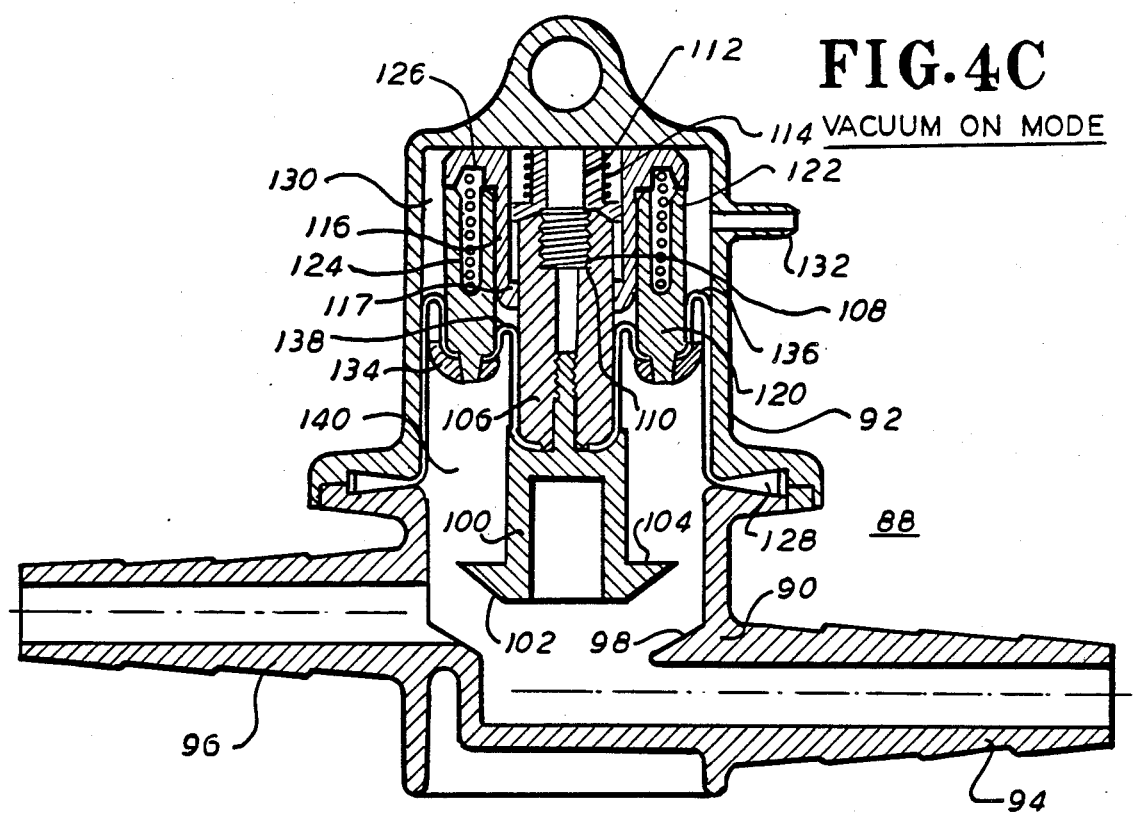
FIG.4C VACUUM ON MODE
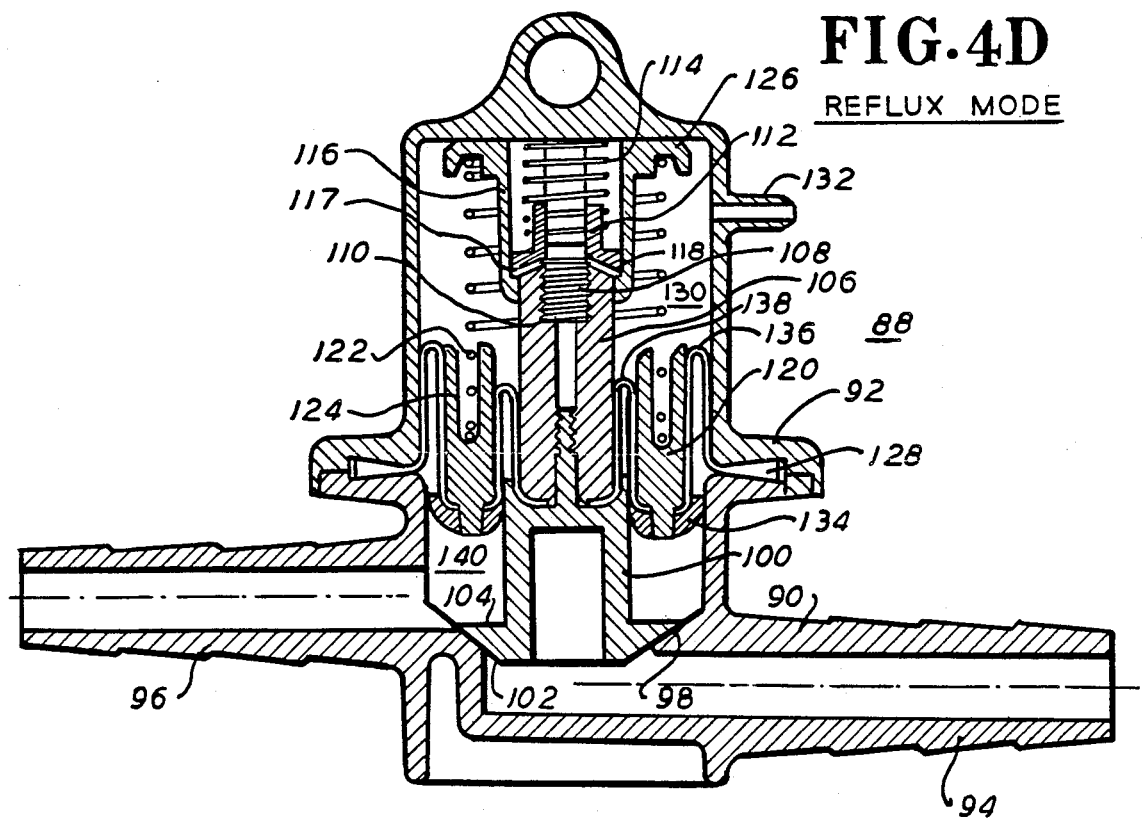
FIG.4D REFLUX MODE

POSITIVE PULSE DEVICE AND SYSTEM

BACKGROUND OF THE INVENTION

This invention relates to a device for the withdrawal of fluids from patient cavities. More specifically, the present invention comprises a device that can be utilized adjacent to or directly upon a catheter used for the withdrawal of such fluids and which operates at predetermined intervals to return, under a positive pressure, a minute quantity of that withdrawn fluid back into the catheter to clear the withdrawal passageways.

Intermittent suction devices are used regularly to remove fluids from patients cavities, such as the stomach, and typically are utilized post-operatively. Such devices can operate from a main source of vacuum that is available in hospital recovery rooms by means of central piping systems.

In non-intermittent suction units, the hospital vacuum system withdraws the fluids continuously into some receiver and discontinues the withdrawing cycle only when the collection container is full or hospital personnel disconnect the system.

With intermittent suction, the continuous withdrawing of fluids is intermittently discontinued at timed intervals. In some units, the vacuum applied by the tubing withdrawing the fluids is cycled to atmospheric pressure so that the portion of the fluid moves backwardly toward the patient in order to clear obstructions in the line or to move the catheter away from the wall of the stomach. One difficulty with such systems is that the back flush is carried out to some extent by gravitational forces and therefore the collection container needed to be located at an elevation higher than the patient. Often such devices are incorporated into the timing apparatus itself on the hospital wall at the height of the receptacle providing the vacuum. In addition, gravity force often was not effective in that the tubing carrying fluid from the patient seldom contained a solid line of liquid but more often carried pockets of gas. A typical device of the type that returned the line withdrawing fluids to atmospheric pressure is shown and described in U.S. Pat. No. 3,659,605 of Ulrich Sielaff.

In an effort to correct some of the problems, positive pulse devices have been proposed and which send a positive quantity of fluid backwards toward the patient to flush the passageways. One of such devices is shown and described in U.S. Pat. No. 4,315,506 to Kayser, et al.

One of the difficulties with the Kayser, et al. device is, however, that it features an expandable reflux chamber actually in the suction line to the patient. That reflux chamber comprises a piston that is withdrawn to expand the reflux chamber and, at the predetermined time interval, the piston moves to collapse the reflux chamber, forcing the contents therein back towards the patient to clear the passageways of obstructions.

By use of a single piston and expandable chamber, however, most of the stroke of the Kayser, et al. piston occurs with the patient line open but the line from the vacuum source closed. Thus, the expanding reflux chamber actually draws a further vacuum on the patient cavity being drained. It is therefore possible to increase the amount of vacuum applied to the patient to an amount in excess of the regulated vacuum established by a doctor as suitable for that patient.

The possibility of the Kayser, et al. device itself actually drawing an excessive vacuum on the patient prevented application of the Kayser, et al. device at or on the catheter to the patient. Such catheters are relatively inflexible and thus the drawing of such vacuum at or near the actual catheter opening would have the most severe effect on that vacuum reaching the patient cavity. Thus, the practical location of the Kayser, et al. device was contemplated to be at the end of the tubing connecting the catheter to other equipment such as the collection bottle. Generally, that tubing was in the order of six (6) feet in length and for convenience, typical tubing for withdrawing fluids is relatively flexible and thus also distensible.

Accordingly, the use of the Kayser, et al. device remote from the actual patient catheter created a reservoir effect in the flexible tubing. The amount of fluid returned to the patient line to clear obstructions therefore had to be relatively large since its effect was dissipated in the reservoir created by the long length of distensible tubing and it was necessary that the returned volume have an effect at the end of the catheter within the patient to clear that catheter from becoming attached to inner walls of the cavity being drained.

Thus the Kayser, et al. device required a relatively large volume, structure and could only be used remote from the patient catheter.

SUMMARY OF THE INVENTION

The present invention overcomes the difficulties of the aforedescribed systems by providing a dual chamber positive pulse device that prevents vacuum to the patient from exceeding, to any great extent, that set by the doctor. In addition, since the positive pulse device of the present invention, protects against excessive vacuum reaching the patient, it can be made much smaller than the Kayser, et al. device and used adjacent or attached to the catheter that enters the patient.

Thus, a system of utilizing a positive pulse can utilized that allows the regulator, collection jar and operating means to be located at some distance remote from the patient, but the positive pulse device that actually delivers the pulse to the patient can be mounted directly on the catheter or very near to the catheter, that is, so that any passages thereafter to the patient cavity are relatively inflexible. Due to its diminished size, the entire positive pulse device can be produced fairly inexpensively, yet efficiently and reliable provide a positive pulse to the patient.

The catheter pulse device is adapted to operate from two sources of vacuum signals, one regulated source is used to reach the patient cavity and is set by an authorized person while the other signal need not be regulated and is used only to control the positive pulse device to expand its reflux chamber. In the preferred embodiment, the latter signal is time delayed such that it will switch to atmospheric pressure a predetermined time period after the regulated vacuum has switched to atmospheric pressure. By utilizing a plurality of chambers in the device itself, the unregulated vacuum signal is isolated in a signal chamber within the positive pulse device and does not reach any passageways connecting to the patient. The positive pulse device contains a valve that controls the regulated vacuum to the patient and which opens a significant amount at or near the point that its expanding reflux chamber draws a vacuum on the patient line approximately equal to the set point of the regulated vacuum. The reflux chamber can therefore continue to expand but without drawing any vacuum on the patient cavity in excess of the regulated vacuum that is intended for that patient.

BRIEF DESCRIPTION OF THE DRAWINGS

The positive pulse device is illustrated in the accompany drawings which show the preferred embodiment of the invention incorporating the features and advantages described.

FIG. 4A is a cross-sectional view of the positive pulse device of the present invention show in the VACUUM OFF mode;

FIG. 4B is a cross-sectional view of the positive pulse device of the present invention in the VACUUM APPLIED FIG. 4C is a cross-sectional view of the positive pulse device of the present invention in the VACUUM ON mode; and FIG. 4D is a cross-sectional view of the positive pulse device of the present invention in the REFLUX mode.

DESCRIPTION OF THE PREFERRED EMBODIMENT

Figure 1:
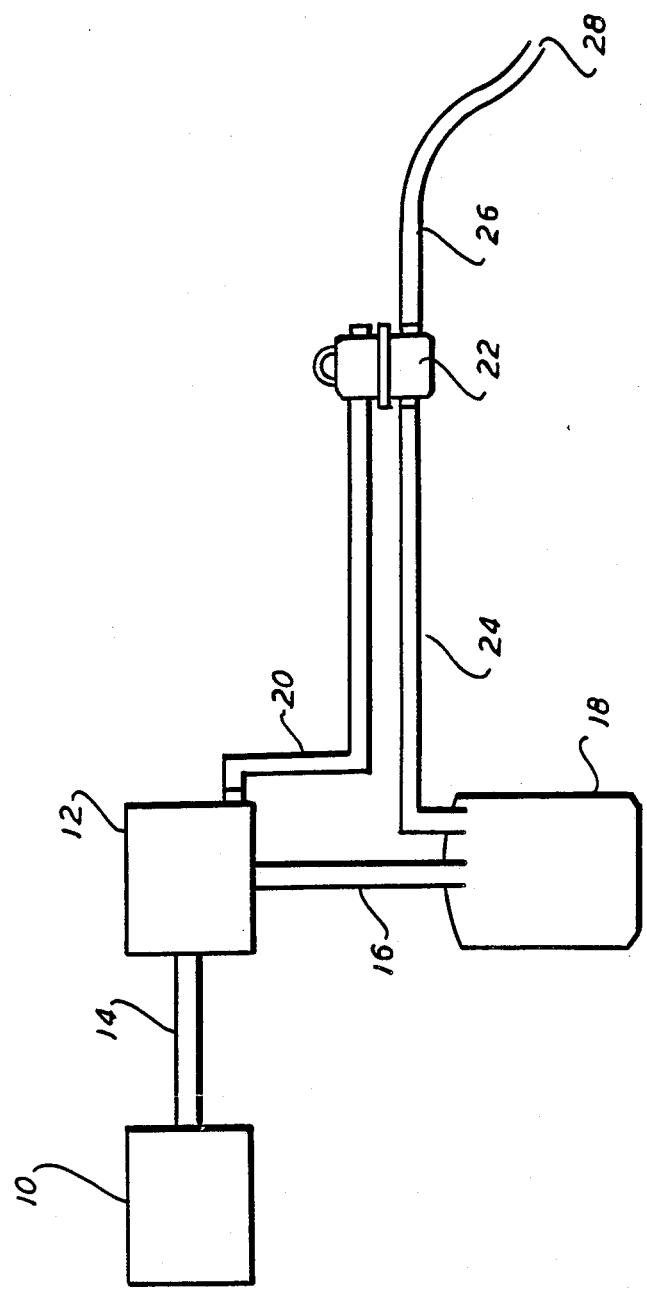
FIG. 1 is a flow diagram showing the positive pulse device of the present invention installed in an intermittent suction circuit and attached to a catheter.

Referring now to FIG. 1, there is shown a flow diagram of a positive pulse suction system and having as a component; the new positive pulse device for removal of fluids from a patient.

A vacuum source 10 provides a regulated vacuum for operation of the suction system. Vacuum sources are relatively common in hospitals and provide a source of vacuum in certain individual hospital rooms from a central vacuum pumping system. The vacuum of such hospital systems typically may range within 300-600 mm Hg.

An intermittent suction control unit or ISU 12 is connected to the vacuum source 10 by suitable connection means such as piping 14. The ISU 12 is typical of the device shown in of U.S. Pat. No. 3,659,605 of Ulrich Sielaff, however, certain modifications to the Sielaff device are made to accommodate the ISU 12 to the particular type of positive pulse device to be later described. The particular ISU 12 used in the present invention has a regulated vacuum line 16 that leads to a collection container 18 that receives the fluids drained from the patient and has a second vacuum signal line 20 that goes directly into the positive pulse device 22 as will be explained.

Also connecting into the positive pulse device 22 is the regulated vacuum line 24. A catheter 26 which is normally relatively inflexible or not distensible also is attached to the positive pulse device 22 and which is placed in the patient such that the open catheter end 28 reaches the fluids desired to be withdrawn. As will be later seen, one of the features of the particular positive pulse device 22 made in accordance with this invention allows it to be positioned at or near the catheter end remote from open catheter end 28 so that only relatively inflexible passageways are between the positive pulse device 22 and open catheter end 28. The further passageway for fluid, regulated vacuum line 24 as well as the vacuum signal line 20 and regulated vacuum line 16 may be standard relatively flexible medical tubing.

Figure 2:
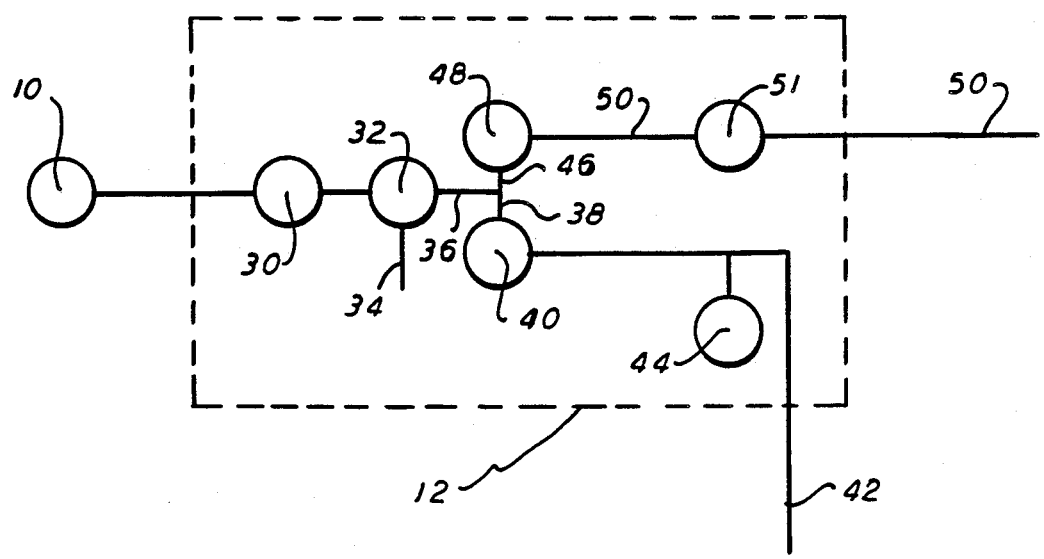
FIG. 2 is a flow diagram of an intermittent suction mechanism used with the present invention.

Turning now to FIG. 2, there is shown a flow diagram of an ISU 12 that can be used in the present invention. The overall purpose of ISU 12 is to provide a regulated vacuum signal for ultimate use with the patient and a second source that need not be regulated and which acts as a vacuum signal for operating the positive pulse device. The present ISU 12 is pneumatically operated, however, the signals could be achieved by electronic switching or other means.

One of the important distinctions between ISU 12 and the intermittent suction unit of the aforementioned Sielaff patent is that ISU 12 includes two (2) vacuum output signals. In its operation, ISU 12 simultaneously supplies vacuum to two (2) outputs, one regulated and one that need not be regulated. During suction at the patient ISU 12 simultaneously supplies vacuum at both outputs and after the duration of the suction cycle, ISU 12 returns the regulated vacuum line, to the patient, to atmospheric pressure. After a predetermined short time interval the other vacuum output is returned to atmospheric pressure.

In FIG. 2, the vacuum source 10 provides the vacuum to ISU 12 as described previously with respect to FIG. 1. That source of vacuum is initially controlled by an "on-off" switch 30 which merely shuts off the vacuum from vacuum source 10 when the unit is not in use. A intermittent device 32 thereafter is controlled by vacuum and may be of the same design as shown in the aforemention Sielaff U.S. Pat. No. 3,659,605. Intermittent device 32 includes an atmospheric vent 34 by which the further lines withdrawing fluids from the patient are intermittently vented to atmospheric pressure.

Tracing now, the source of vacuum that ultimately reaches the patient, the intermittent vacuum/atmospheric pressure signal from intermittent device 32 proceeds via passages 36 and 38 to a vacuum regulator 40 where the doctor, or other qualified personnel, actually sets the maximum level of vacuum that the patient can experience. The vacuum regulator 40 is conventional and thereafter the regulated vacuum proceeds by passage 42 to connect with regulated vacuum line 16 to collection container 18 (FIG. 1). A vacuum gauge 44 is in the passage 42 so that the doctor can verify and continually monitor that the regulated vacuum from ISU 12 is at the desired set point.

Returning to the intermittent device 32, the same intermittent vacuum/atmospheric pressure signal proceeds via passages 36 and 46 to a pause valve 48 where a predetermined time delay is created between the time that the signal from intermittent device 32 goes from vacuum to atmospheric pressure and the time that signal from the output of pause valve 48 to passage 50 goes from vacuum to atmospheric pressure, as will be latter explained. The passage 50 connects to vacuum signal line 20 of FIG. 1 and is used to control the positive pulse device 22. A liquid safety trap 51 is provided in passage 50 in order to prevent liquid from returning and entering pause valve 48.

Of the components of ISU 12, the pause valve 48 is not conventional and therefore will be described in further detail.

Figure 3A:
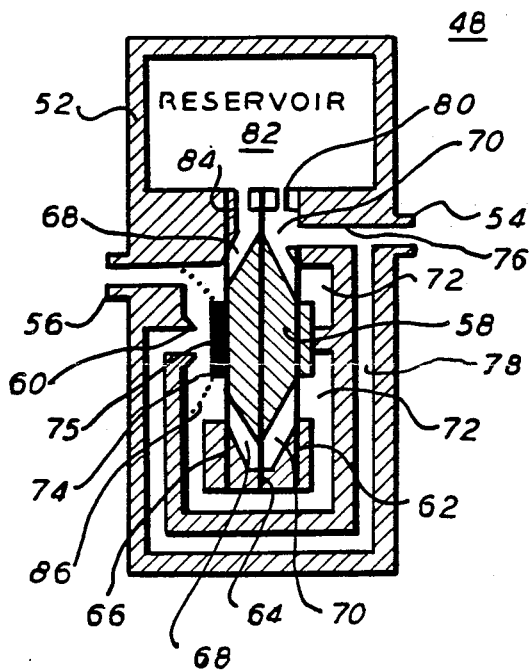
FIG. 3A is a cross-sectional view of a pause valve used with the intermittent suction mechanism of FIG. 2.
Figure 3B:
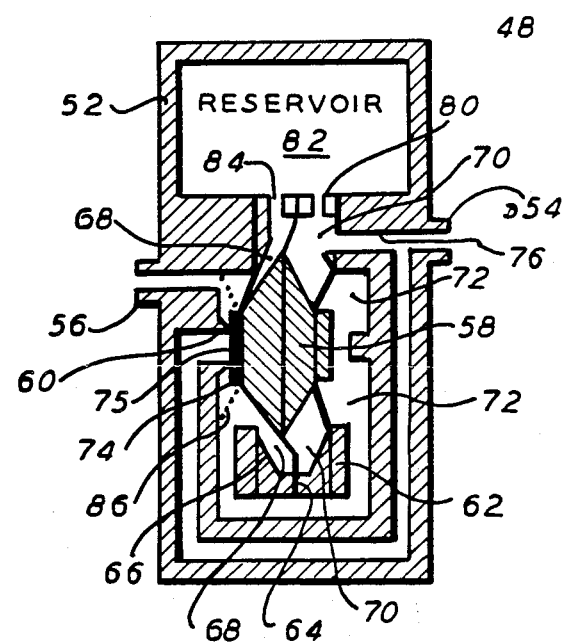
FIG. 3B is a cross-sectional view of the pause valve of FIG. 3A in its alternate position; mode.

Turning now to FIGS. 3A and 3B, there is shown cross-sectional views of the pause valve 48 which may be used with the present invention. Pause valve 48 comprises a housing 52, preferably of a plastic material having an inlet 54 which connects to passage 46 of FIG. 2 which is the intermittent vacuum/atmospheric pressure signal from the intermittent device (FIG. 2) and an outlet 56 which, in turn, connects to passage 50 of FIG. 2 and thereafter to the positive pulse device 22 (FIG. 1) and provides the vacuum signal therefore. Within housing 52 of pause valve 48 is a moveable valve member 58 and a valve seat 60. The moveable valve member 58 is retained within housing 52 by three diaphragms 62, 64 and 66 and which form various chambers in order that various levels of vacuum and/or atmospheric pressure influence the movement and position of moveable valve member 58. The diaphragms 62, 64 and 66 specifically divide the interior of the pause valve 48 into pilot chambers 68, 70 and main chambers 72 and 74.

Moveable valve member 58 additionally has a resilient pad 75 that seals against valve seat 60 when in the valve closed position of FIG. 3B. As shown in FIG. 3A, the moveable valve member 58 is in the valve open position and resilient pad 75 is not seated against valve seat 60.

Various passages are formed in housing 52, passage 76 communicates directly between inlet 54 and pilot chamber 70 while passage 78 is a longer passage than passage 76 and provides communication between inlet 54 and main chamber 74, the purpose of passage 78 being longer or having more resistance than passage 76 will become clear.

The pilot chambers 68 and 70 also are in communication between each other through a fixed orifice 80 which extends between pilot chamber 70 and reservoir 82 and by passage 84 between reservoir 82 and the other pilot chamber 68, otherwise pilot chambers 68 and 70 are isolated from each other by diaphragm 64. A spring 86 biases the moveable valve member 58 toward its valve open position as shown in FIG. 3A.

Taking now the operation of the pause valve 48, it should be reminded that the purpose thereof is to introduce a short delay between the time that the vacuum signal at its inlet 54 goes to atmospheric pressure and the time that the vacuum signal at its outlet 56 goes to atmospheric pressure. As seen in FIG. 2, the delay occurs such that when the vacuum in passage 36 switches from vacuum to atmospheric pressure by the intermittent device 32, the regulated vacuum in passage 42 leading to the patient immediately also switches from vacuum to atmospheric pressure while the signal in passage 50 is delayed slightly before it switches from vacuum to atmospheric pressure. Both signals, that in passage 36 and 42 are, however, controlled by intermittent device 32.

Returning to FIGS. 3A and 3B, the cycle can be commenced with all chambers, that is pilot chambers 68, 70 and main chambers 72 and 74 at atmospheric pressure and the valve is in the valve open position of FIG. 3A. As vacuum is applied to inlet 54 when the intermittent device 32 commences its vacuum or suction cycle, the vacuum immediately reaches pilot chamber 70, thereby reinforcing the bias of spring 86 and retaining the moveable valve member 58 in the position shown in FIG. 3A. The vacuum also communicates through passage 78 to draw a vacuum in main chambers 74 and 72. At this point, therefore, vacuum is drawn at outlet 56 and pilot chamber 70 as well as main chambers 74 and 72 so that all chambers except pilot chamber 68 are at the high vacuum seen at the inlet 54. As time passes, the reservoir 82 is slowly evacuated through fixed orifice 80 such that over a predetermined time period, pilot chamber 68 also reaches high vacuum. At this point, all of the chambers 68, 70, 72 and 74 are at high vacuum.

As the intermittent device 32 switches to its atmospheric pressure mode, the pressure at inlet 54 immediately goes to atmospheric pressure and atmospheric pressure is simultaneously communicated to pilot chamber 70 through passage 76. The main chambers 72 and 74 are balanced in surface area and high vacuum pressures, the pilot chambers 68 and 70 are unbalanced; high vacuum in pilot chamber 68 and atmospheric pressure in pilot chamber 70. This overcomes the force of spring 86 and moves the pause valve 48 to its position shown in FIG. 3B causing resilient pad 75 to close against valve seat 60. Since the passage 78 is relatively long and restricted, the valve seat 60 is closed by resilient pad 75 before atmospheric pressure can travel through passage 78 to reach main chamber 74. Thus, at this point in time, only the pilot chamber 70 and passages 76 and 78 are at atmospheric pressure while main chambers 72, 74 and the reservoir 82 and pilot chamber 68 are still at high vacuum.

Reservoir 82, however, slowly returns to atmospheric pressure by dissipation of its vacuum through atmospheric pressure entering through fixed orifice 80. As reservoir 82 returns to atmospheric pressure, so does pilot chamber 68. When pilot chamber 68 reaches atmospheric pressure, the pressure related forces on moveable valve member 58 become equal since both pilot chambers are at atmospheric pressure and the areas through which that atmospheric pressure acts upon moveable valve member 58 are equal. The main chamber 72 and 74 are both still at high vacuum and the respective areas acting upon moveable valve member 58 are also equal, thus the only additional force acting upon moveable valve member 58 is the bias of spring 86 which is the resultant force and which moves the moveable valve member 58 back to its valve position position shown in FIG. 3A.

As the moveable valve member 58 moves to the FIG. 3A position, the passage through valve seat 60 also opens such that main chambers 72 and 74 are returned to atmospheric pressure and therefore the outlet 56 returns to atmospheric pressure. Thus a time delay is introduced between the time the inlet 54 is vented to atmospheric pressure and the time that atmospheric pressure appears as a signal at outlet 56.

Obviously, the actual pause time is a matter of design and depends upon the characteristics of spring 86, the volume of reservoir 82, the vacuum levels applied and the size of orifice 80.

Turning now to FIGS. 4A-4D, there is shown a positive pulse device 22 made in accordance with the present invention and in its four (4) basic positions respectively, the VACUUM OFF, the VACUUM APPLIED mode, the VACUUM ON mode, and the REFLUX mode.

Taking FIG. 4A first, the positive pulse device 22 comprising a housing 88 which is conveniently made up of lower housing 90 and upper housing 92 which are joined together as will be explained. Housing 88 has an inlet 94 which is connected to the collection chamber 18 (see FIG. 1) and therefore is connected to the source of regulated vacuum. An outlet 96 is also formed in housing 88 and is adapted to be connected directly or adjacent to a patient catheter. A valve means is interposed between inlet 94 and outlet 96 and is formed by valve seat 98 and moveable valve member 100 that moves into engagement with valve seat 98 or away therefrom to control the flow between inlet 94 and outlet 96. Moveable valve member 100 has a truncated conical shape surface 102 that mates with valve seat 98 and which also forms an annular ridge 104 facing upwardly away from valve seat 98.

Moveable valve member 100 includes a valve extension 106 that depends upwardly and which is sonic welded to the lower part of moveable valve member. A spring bias is provided by a small spring 108 and which acts to bias the moveable valve member 100 toward its closed position against valve seat 98. This spring bias is very small, however, and is created by the preload effected by installing small spring 108 with lower end of small spring 108 seating on inner ledge 110 formed in the valve extension 106 and its upper end held by the lower end of moveable cap 112. Moveable cap 112, in turn, is biased toward valve extension 106 by medium spring 114 which acts against a flange 114 of moveable cap 112 having its other end seated against the top of housing 88. The moveable cap 112 is contained within a keeper 116 which retains the moveable cap 112 in position and limits its downward movement by an inner ledge 117. As noted in FIG. 4A, in the VACUUM OFF mode, the moveable cap 112 at its lowermost position does not directly touch the upper end of valve extension 106 in its lowermost position. Instead a gap 118 of about 0.040 inches is retained between the bottom of moveable cap 112 when it is in its lowermost position and the top of valve extension 106 when it is in its lowermost position. As will become clear, the spring constant or bias exerted by medium spring 114 is higher than that of small spring 108.

Surrounding moveable valve member 100 is an annular piston 120 that moves independent of moveable valve member 100, however, in the position of FIG. 4A, annular piston 120 directly engages the annular ridge 104 of moveable valve member 100 and urges the moveable valve member 100 toward its closed position by the bias of large spring 122 which is precompressed and has its lower end held within annular groove 124 in annular piston 120 and its other end abuts against the top of housing 88 and held in position by spring keeper 126. Thus, in the VACUUM OFF mode of FIG. 4A, the large spring 122 acts as an additional force in retaining the moveable valve member 100 in its closed position against valve seat 98.

A diaphragm 128 creates a control chamber 130 in the upper housing 92 and which control chamber 130 is sealed except for control port 132 which is adapted to be connected to vacuum signal line 20 (shown in FIG. 1). Diaphragm 128 has its outer peripheral edge secured in housing 88 by being sandwiched between lower housing 90 and upper housing 92 which may be sonic welded together. Diaphragm 128 has its inner edge sealed to moveable valve member 100 by the connection of the valve extension 106 to the lower part thereof, again which may be a sonic welded connection. Intermediate its outer periphery and its inner edge, diaphragm 128 is also sealed to annular piston 120, which seal may be effected by compressing the diaphragm 128 against annular piston 120 by means of annular cap 134 which also may be sonic welded to annular piston 120.

As shown, the diaphragm 128 is a single piece of flexible material, however, it may readily be made up of two (2) separate diaphragms while still carrying out the purpose of forming a pair of rolling seals, that is, an outer rolling seal at 136 and an inner rolling seal at 138.

Each of the rolling seals 136 and 138 allow independent movement of moveable valve member 100 and annular piston 120 with respect to each other and yet retain the integrity of the control chamber 130.

Referring now to FIG. 1 as well as FIGS. 4A-4D, the operation of the positive pulse device 22 can be readily understood. Initially, at start-up, the positive pulse device 22 is in the position as shown in FIG. 4A. At this point in the cycle, the inlet 94, outlet 96 and the control part 32 are all at atmospheric pressure. The valve means is closed since moveable valve member 100 is in its lowermost position sealed against valve seat 98, so there is no communication between the inlet 94 and outlet 96. The moveable valve member 100 is retained in that position, being held there by the annular piston 120 acting against annular ridge 104 and biased by large spring 122 and by the bias of the small spring 108. Both large spring 122 and small spring 108 are, of course, preloaded. The catheter 26, and therefore outlet 96 may, at times, be slightly above atmospheric pressure due to positive tissue pressure in the stomach, however any drainage that might occur due to gravity or differential pressure forces is prevented by the closed valve means.

Taking, now, the VACUUM APPLIED mode of FIG. 4B, the FIG. 4B depicts the positive pulse device 22 slightly after the ISU 12 has switched from atmospheric pressure to vacuum mode and two (2) levels of vacuum are being applied to the positive pulse device 22. Regulated vacuum is being applied to the inlet 94 and vacuum that need not be regulated, the pipeline vacuum level of the particular hospital system, is being applied to control part 132 by means of vacuum signal line 20.

Initially, as those vacuum levels are applied, the unregulated vacuum in the control chamber 130 creates a negative resultant force on the annular piston 120 since the lower surface of annular piston 120 is at or near atmospheric pressure since outlet 96 of the positive pulse device 22 is at atmospheric pressure. The moveable valve member 100 is still closed and therefore the regulated vacuum at inlet 94 does not affect that resultant force since it cannot reach outlet 96.

Accordingly, the negative resultant force on annular piston 120 causes it to move upward away from the valve seat 98 and lifts off of its contact with annular ridge 104 of moveable valve member 100. The spring bias exerted against moveable valve member 100 by large spring 122 is therefore eliminated and the moveable valve member 100 is retained in its closed position against valve seat 98 by whatever differential pressure forces exist and by means of the rather small bias exerted by small spring 108. As the annular piston 120 continues to move upward, collapsing the control chamber 130, it draws a vacuum at the outlet 96 and thus on the patient through catheter 26. A reflux chamber 140 beneath the diaphragm 128, is created and expands, separated, of course from the unregulated vacuum in the control chamber 130. Eventually, the annular piston 120 creates a sufficient vacuum at outlet 96 to approximately equal the regulated vacuum already applied to the inlet 94, and at this point, the forces acting upon the moveable valve member 100; that is, the unregulated vacuum in control chamber 130, regulated vacuum in the inlet 94, at or near regulated vacuum in outlet 96 and the small bias of small spring 108 cause the moveable valve member 100 to withdrawn from the contact with valve seat 98 and cracks that valve means between inlet 94 and outlet 96 allowing the regulated vacuum from regulated vacuum line 24 to reach the catheter 26. Thus the regulated vacuum prescribed for that particular patient is applied to the patient cavity to be drained and no higher vacuum reaches the patient despite further travel of the annular piston 120 or moveable valve member 100.

It should be noted that the position of the positive pulse device 22 shown in FIG. 4B is such that the moveable valve member 100 has merely overcome the relatively small bias of small spring 108 and thus movement of moveable valve member 100 away from valve seat 98 closes the gap 118. The moveable valve member 100 has moved approximately 0.040 inches, away from valve seat 98 sufficient to crack the valve means. Further movement away from valve seal 98 by moveable valve member 100 is thereafter resisted by the larger bias of medium spring 114.

Although the regulated vacuum is at this time being applied to the patient through catheter 26, both the moveable valve member 100 and annular piston 120 continue to retract away from valve seat 98, however both move at approximately the some rate since both are acted upon by about the same forces. On the annular piston 120, a differential force is created by the difference between the unregulated vacuum in control chamber 130 acting on the annular area of annular piston 120 and the regulated vacuum in inlet and outlets 94 and 98 acting on the annular area of annular piston 120 in addition to the force of large spring 122. On the moveable valve member 100, a differential force is created by the difference between the unregulated vacuum in control chamber 130 acting on the upper area of moveable valve member 100 and the force of both the medium spring 114 and the small spring 108 and the regulated vacuum in the inlet and outlet 94 and 96 acting against the lower area of moveable valve member 100. Eventually, both the moveable valve member 100 and annular piston 120 reach their fully retracted positions shown in FIG. 4C and the valve means is fully open applying regulated vacuum to the patient to carry out the drainage.

FIG. 4C shows the VACUUM ON mode where unregulated or full line vacuum is applied to control part 132 retaining the now collapsed control chamber 130 at full line vacuum to hold annular piston 120 and moveable valve member 100 in their fully retracted positions compressing large spring 122, medium spring 114 and small spring 108. Regulated vacuum is continuously applied to the patient from inlet 94 to outlet 96 and thus to catheter 26 and gases and other fluids can be withdrawn through the fully open valve means to be collected in collection container 18.

The positive pulse device continues in its position of FIG. 4C until the ISU 12 switches to release the vacuum signal in passage 36 of FIG. 2 to atmospheric pressure. As previously described, initially only the regulated vacuum in regulated vacuum lines 16 and 24 are vented to atmospheric pressure and thus the inlet 94, outlet 96 and patient via catheter 26 are immediately revented to atmospheric pressure. After a few seconds delay, the vacuum signal line 20 applied to control part 132 and therefore control chamber 130 is also vented to atmospheric pressure. The control chamber 130 returns to atmospheric pressure as does the reflux chamber 140 and the inlet 94 and outlet 96; thus the combined forces on the moveable valve member 100 and annular piston 120 by means of the large spring 122, medium spring 114 and small spring 108 cause the moveable valve member 100 and annular piston 120 to move toward valve seat 98. As can be noted on FIG. 4C, the length of travel of the moveable valve member 100 is relatively short compared with the stroke of annular piston 120 and thus the moveable valve member 100 quite rapidly seats against the valve seat 98 closing the valve means and thus shutting off flow between outlet 96 and inlet 94 and isolating reflux chamber 140 from inlet 94.

As shown in FIG. 4D, the valve means is closed, yet the annular piston 120 still has remaining stroke and as it continues to move toward the valve seat 98 the reflux chamber 140 is collapsed and the fluid within reflux chamber 140 is forced backwardly out of the outlet 96 toward the catheter 26 and the patient. Since the moveable valve member 100 is closed, all of the fluid remaining in reflux chamber 140 is thus forced out the outlet to clear the passageways in the catheter. As the reflux chamber 140 is completely collapsed, the annular piston 120 again seats on the annular ridge 104 of the moveable valve member 100 so that the bias of large spring 122 again acts to retain the valve means closed and the cycle is completed, to be continuously repeated as the ISU 12 continues on to further cycles.

I claim:

1. A positive pulse device for use in a system for withdrawing fluids from a patient cavity and for selectively returning a portion of the withdrawn fluids back toward the patient cavity to clear obstructions, said device comprising;
    (a) a housing, a patient catheter said housing having an inlet for connection to a regulated vacuum source and an outlet means for connection to said a patient catheter in place in a patient cavity,
    (b) valve means in said housing intermediate said inlet and said outlet means, said valve means being normally closed,
    (c) a reflux chamber within said housing formed between said valve means and said outlet means,
    (d) means to expand said reflux chamber at predetermined intervals to withdraw fluid from said outlet and to draw a vacuum at said outlet means,
    (e) means to initially open said valve means a predetermined distance at or prior to the vacuum level at said outlet means reaching a predetermined amount to allow vacuum from the regulated source of vacuum to reach the patient cavity,
    (f) means to close said valve means after a predetermined period of time,
    (g) means to collapse said reflux chamber after closing said valve means to force fluid contained in said reflux chamber back through said outlet to the patient cavity.

2. A positive pulse device as defined in claim 1 wherein said valve means opens when said vacuum drawn at said outlet is approximately the level of vacuum of the regulated vacuum source.

3. A system adapted to be connected to a catheter introduced into a patient cavity for applying suction for withdrawing fluids from the patient cavity and for returning, at predetermined intervals, a portion of the withdrawn fluid back towards the patient cavity under a positive pressure, said system comprising;
    (a) a catheter, a positive pulse device having means located at or adjacent said catheter communicating with the patient cavity, and having an inlet for connecting to a regulated source of vacuum and an outlet for connetion to said catheter, (b) valve means in said positive pulse device intermediate said inlet and said outlet controlling the flow of fluid therethrough, and based toward its closed position by a first bias means, (c) a reflux chamber in said positive pulse device adapted to be selectively expanded to withdraw a portion of fluid from the patient, said expansion drawing a vacuum, (d) means responsive to reaching a predetermined vacuum at said outlet to overcome said first bias means to open said valve means a predetermined distance to allow vacuum from the regulated source of vacuum to reach the implement to prevent vacuum in the patient cavity from exceeding the vacuum from the regulated source, (e) means to continue opening said valve against a second bias means and to continue expanding said reflux chamber, (f) means to selectively collapse said reflux chamber to force fluid contained therein back through said outlet and said catheter to the patient cavity.

4. A system as defined in claim 3 wherein said first bias is a spring of known spring constant and said second bias is a spring of known spring constant higher than the spring constant of said first bias.

5. A system adapted to be connected to a catheter introduced into a patient cavity for applying suction for withdrawing fluids from the patient cavity and for returning, at predetermined intervals, a portion of the withdrawn fluid back towards the patient cavity under a positive pressure, said system comprising;

(a) a catheter, a positive pulse device having means located at or adjacent said catheter communicating with the patient cavity, and having an inlet for connecting to a regulated source of vacuum and an outlet for connection to said catheter, (b) valve means in said positive pulse device intermediate said inlet and said outlet, said valve means comprising a valve seat and a movable valve member movable between an open and a closed position, (c) bias means biasing said movable valve member towards its closed position, (d) a reflux chamber in said positive pulse device intermediate said valve means and said outlet, adapted to be selectively expanded and contracted, (e) actuator means for expanding and contracting said reflux chamber and for moving said movable valve member of said valve means, (f) said actuator means being responsive to a firt signal to expand said reflux chamber to withdraw fluid through said outlet and to draw a vacuum on said outlet, (g) means responsive to reaching a predetermined vacuum at said outlet to overcome said bias means to open said valve means to allow vacuum from the regulated source of vacuum to reach the implement to prevent vacuum in the patient cavity from exceeding the vacuum from the regulated source, (h) said actuator means further responsive to a second signal to move said moveable valve member to its closed position and to collapse said reflux chamber when said valve means is closed to force fluid contained in said reflux chamber back through said outlet toward the patient cavity.

6. A system as defined in claim 5 wherein said first signal is a vacuum signal and said second signal is an atmospheric pressure signal.

7. A system as defined in claim 5 wherein said predetermined vacuum drawn at said outlet to overcome said bias means is about the level of vacuum at said inlet from the regulated source.

8. A system as defined in claim 7 wherein a second bias of an amount larger than said bias, said second bias biasing said moveable valve member toward its closed position during said major proportion of its total expansion after opening of said valve means.

9. A system operably from a vacuum system connected to a catheter introduced into a patients cavity for applying suction for withdrawing fluids from the patient cavity and for returning at predetermined intervals, a portion of the withdrawn fluid back towards the patient cavity under a positive pressure, said system comprising;

(a) a catheter, a positive pulse device having means located at or adjacent said catheter entering the patient cavity, said positive pulse device having an outlet for connection to said catheter, an inlet, and a valve means intermediate said inlet and said outlet and said catheter for controlling the flow of fluid there between, and biased toward its closed position, (b) control means adapted to be connected to the vacuum system, said control means providing a plurality of vacuum and atmospheric pressure signals at predetermined time intervals, (c) first passage means connecting said signals from said control means to said inlet of said positive pulse device, (d) an expandible and contractible reflux chamber in said positive pulse device fluidly connected between said valve means and said outlet, (e) an actuator means for controlling the position of said valve means and for controlling the expansion and contraction of said reflux chamber, (f) second passage means connecting said signals from said control means to said actuator means, (g) said actuator means responsive to a first signal provided from said control means through said second passage to expand said reflux chamber initially when said valve means is closed, said expansion of said reflux chamber drawing a vacuum at said outlet, (h) means responsive to reaching a predetermined vacuum at said outlet to overcome the bias on said valve means to slightly open said valve means to allow vacuum in said first passage to be applied to the implement, (i) said actuator means further responding to said first signal from said control means to further open said valve means and expand said reflux chamber simultaneously, (j) said actuator means being responsive to a second signal from said control means to sequentially close said valve means and thereafter collapse said reflux chamber to force fluid in said reflux chamber back through said outlet and said catheter toward the patient.

10. A system as defined in claim 9 wherein said first signal provided from said control means is a vacuum signal.

11. A system as defined in claim 10 wherein said second signal is an atmospheric pressure signal.

12. A system as defined in claim 9 wherein said actuator is an expandable contractible control chamber isolated from said reflux chamber by a flexible diaphragm, said control chamber adapted to contract to expand said reflux chamber and to expand to contract said reflux chamber.

13. A system as defined in claim 12 wherein said first signal is a vacuum signal and which contract said signal and which contract said control chamber and expands said reflux chamber and said second signal is an atmospheric pressure signal and which expands said control chamber and contracts said reflux chamber.

14. A method of returning a portion of fluids back through a passage removing fluids from a patient comprising the steps of:

(a) providing a catheter having a passage and a valve means in the passage removing the fluids to control the flow therethrough, (b) providing an expandable chamber communicating with said passage in a position on the patient side of the valve.

(c) expanding the expandable chamber while retaining the valve closed, to withdraw fluid from the patient and to draw a vacuum at the patient, (d) opening the valve prior to or upon sensing a predetermined level of vacuum drawn on the patient, (e) holding the valve open while continuing to expand the expandable chamber holding the valve open and chamber fully expandable for a predetermined amount of time, (f) closing the valve after that predetermined amount of time, and collapsing the expanded chamber to force fluid contained therein back toward the patient.

* * * * *

UNITED STATES PATENT AND TRADEMARK OFFICE
CERTIFICATE OF CORRECTION

PATENT NO. : 4,767,403
DATED : August 30, 1988
INVENTOR(S) : C. G. Hodge

It is certified that error appears in the above-identified patent and that said Letters Patent is hereby corrected as shown below:

Column 3, line 17, "mode;" should be deleted.

Column 3, line 23, should be "VACUUM APPLIED mode;" not just "VACUUM APPLIED".

Column 7, line 26, there should not be a dash between "not-directly".

Column 11, line 3, "based" should be "biased".

Signed and Sealed this

Twenty-ninth Day of August, 1989

Attest:

DONALD J. QUIGG

Attesting Officer

Commissioner of Patents and Trademarks